United States Patent [19]

Yamabe et al.

[11] 4,362,672
[45] Dec. 7, 1982

[54] PROCESS FOR PRODUCING DIFLUOROHALOACETYL FLUORIDE

[75] Inventors: Masaaki Yamabe, Machida; Seiji Munekata; Shunichi Samejima, both of Tokyo, all of Japan

[73] Assignee: Asahi Glass Company, Ltd., Tokyo, Japan

[21] Appl. No.: 286,974

[22] Filed: Jul. 27, 1981

[30] Foreign Application Priority Data

Aug. 26, 1980 [JP] Japan ................ 55-116403

[51] Int. Cl.$^3$ ............................ C07C 51/58
[52] U.S. Cl. ................ 260/544 F; 260/456 R
[58] Field of Search ......... 260/456 R, 456 F, 456 NS, 260/544 F

[56] References Cited

U.S. PATENT DOCUMENTS

| | | | |
|---|---|---|---|
| 2,676,983 | 4/1954 | Hurka | 260/544 F |
| 3,052,717 | 9/1962 | Regan | 260/544 F |
| 3,689,545 | 9/1972 | Hahn et al. | 260/544 F |
| 3,725,475 | 4/1973 | Paucksch et al. | 260/544 F |
| 3,862,971 | 1/1975 | Rudolph et al. | 260/544 F |
| 4,318,867 | 9/1982 | Yamabe et al. | 260/544 F |

FOREIGN PATENT DOCUMENTS 2052501 1/1981 United Kingdom ............ 260/544 F

*Primary Examiner*—Natalie Trousof
*Assistant Examiner*—Leah Hendriksen
*Attorney, Agent, or Firm*—Oblon, Fisher, Spivak, McClelland & Maier

[57] ABSTRACT

A difluorohaloacetyl fluoride is produced by (a) producing an intermediate having a group of the formula $$XCF_2CFYOSO_2{}^-$$

wherein X is I or Br, Y is F, Cl, Br or I; by reacting a polyfluoroethylene of the formula $$CF_2=CFY$$

with a reagent obtained by mixing sulfur trioxide with a halogen selected from iodine and bromine; and (b) decomposing said intermediate into said product.

11 Claims, No Drawings

PROCESS FOR PRODUCING DIFLUOROHALOACETYL FLUORIDE

BACKGROUND OF THE INVENTION

1. FIELD OF THE INVENTION

The present invention relates to a process for producing difluorohaloacetyl fluoride ($XCF_2COF$: $X = I$ or Br) which is useful as an intermediate for various fluorine-containing compounds or a compound having special characteristics. For example, difluorohaloacetyl fluoride can be converted into ω-haloperfluorocarbon vinyl ether an useful intermediate for thermosetting fluorinated resins, first by adding hexafluoropropylene oxide and then pyrolyzing the resulting adduct. Difluorohaloacetyl fluoride can also be converted into perfluorosuccinyl fluoride by a coupling reaction accomplished by dehalogenation. The resulting perfluorosuccinyl fluoride reacts to give perfluorodicarboxylic acid derivatives by a reaction with a neucleophilic reagent. The derivatives serve to be useful intermediate for fluorine-containing condensation polymers such as polyamides and polyesters having excellent thermal resistance and chemical stability. The difluorohaloacetyl fluorides also serve as a starting material for perfluoro (3-oxa-4-pentenoyl fluoride) or oxalyl fluoride, both of which are useful as intermediates for various fluorine-containing compounds.

DESCRIPTION OF THE PRIOR ART

The only known process for producing difluoroiodoacetyl fluoride is to react tetrafluoroethylene oxide with anhydrous lithium iodide in acetic anhydride. (Japanese Examined Patent Publication No. 8205/1970). However, in the known process, it is necessary to use tetrafluoroethylene oxide which is difficult to produce because of its high potential of explosion and low production yield. Moreover, in this process the yield of difluoroiodoacetyl fluoride based on tetrafluoroethylene oxide is at maximum 40%. Thus, it is not satisfactory for an industrial operation.

On the other hand, as regards to a process for producing difluorobromoacetyl fluoride the preparation of difluorobromoacetate has been known by first heating a mixture of 1,2-dibromochlorotrifluoroethane and fuming sulfuric acid having 40% sulfur trioxide content in the presence of mercury oxide followed by the reaction of the resulting gas with an alcohol. (Tetrahedron. 33, 1445 (1977)). However, when said process is employed for the production of difluorobromoacetyl fluoride, a special purification is required for separating difluorobromoacetyl fluoride from difluorobromoacetyl chloride which is not easily separated from difluorobromoacetyl fluoride since a large amount of difluorobromoacetyl chloride is included in the resulting gas. Moreover, mercury oxide which is included in the reaction system is highly toxic and accordingly, a special treatment is required. Therefore, the process is not satisfactory for an industrial operation.

It has been also proposed to produce difluoroacetyl fluorides by an oxidation of 1-bromo-2-iodo-tetrafluoroethane with an oxidizing acid or by a bromination of difluoroiodoacetyl fluoride. These processes require several reaction steps for producing the starting materials to result in multi-step reactions in total. Therefore, these processes are not satisfactory for an industrial operation.

SUMMARY OF THE INVENTION

It is an object of the present invention to provide a process for producing a difluorohaloacetyl fluoride at a high yield by a simple operation.

The foregoing and other object of the present invention have been attained by producing a difluorohaloacetyl fluoride which comprises the steps of:

(a) producing an intermediate having a group of the formula

$XCF_2CFYOSO_2—$ wherein X is I or Br, Y is F, Cl, Br or I; by reacting a polyfluoroethylene of the formula

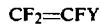
$CF_2=CFY$ with a reagent obtained by mixing sulfur trioxide with a halogen selected from iodine and bromine; and (b) decomposing said intermediate into said product.

DETAILED DESCRIPTION OF THE PREFERRED EMBODIMENTS

The present invention has been attained through various studies involving the afore-mentioned problems, and it is found that a stable intermediate having $XCF_2CFYOSO_2—$ group wherein X represents I or Br and Y represents F, Cl, Br or I is produced by reacting a specific polyfluoroethylene with a specific reagent at a high yield and difluorohaloacetyl fluoride can be obtained at a high yield through a decomposition reaction of the intermediate.

In the process of the present invention, it is important to use polyfluoroethylene having the formula $CF_2=CFY$ as a starting material and a mixture of a halogen of iodine or bromine and sulfur trioxide as a reagent mixture. In this combination, an intermediate having $XCF_2CFYOSO_2—$ group which can be converted into difluorohaloacetyl fluoride can be produced at a high yield and accordingly, difluorohaloacetyl fluoride can be obtained at a high yield.

The polyfluoroethylene having the formula $CF_2=CFY$ used in the present invention include four compounds; $CF_2=CF_2$ (tetrafluoroethylene); $CF_2=CFCl$ (chlorotrifluoroethylene); $CF_2=CFBr$ (bromotrifluoroethylene); and $CF_2=CFI$ (iodotrifluoroethylene). One or more of the compounds can be used separately or as a mixture. Among the polyfluoroethylene, tetrafluoroethylene and chlorotrifluoroethylene are preferably chosen from their commercial availability. Tetrafluoroethylene with its symmetrical structure is most preferred, in considering the selectivity of the reaction.

In the process of the present invention, the reagent mixture of a halogen and sulfur trioxide can be used just after mixing or also after a partial reaction of the halogen with sulfur trioxide has taken place. The reagent mixture can be prepared either in a separate reactor or in the same reactor prior to the reaction of the reagent mixture with the polyfluoroethylene.

The molar ratio of sulfur trioxide to a halogen is not critical in the preparation of the reagent mixture. In the reaction of the reagent mixture with a polyfluoroethylene, when the molar ratio is too low, dihalopolyfluoroethane which is an adduct of the polyfluoroethylene and the halogen is produced as a by-product. On the other hand, when the molar ratio is too high, sultone which is an adduct of the polyfluoroethylene and sulfur trioxide is produced as a by-product. Therefore, it is preferable to select the molar ratio in the range of 1 to 5.

The preparation of the reagent mixture can be carried out in the absence of a solvent as well as in the presence of a solvent such as 1,1,2-trichlorotrifluoroethane and 1,2dibromotetrafluoroethane.

It is preferable to prepare the reagent mixture under substantially anhydrous condition.

When the temperature in the reaction of the polyfluoroethylene with the reagent mixture is too low, the reagent mixture solidifies or the reaction rate is lowered considerably. On the contrary, when the temperature is too high, an unfavorable side reaction such as decomposition becomes significant. Therefore, the reaction is preferably carried out at a temperature of $-50°$ C. to $+300°$ C. especially from $-20°$ C. to $+150°$ C. The reaction pressure is not critical. The reaction can be carried out under a pressure of up to 50 kg/cm$^2$ gauge as well as under reduced pressure.

The molar ratio of the polyfluoroethylene to the reagent mixture is preferably in the range of 0.2:1 to 10:1 especially from 0.5:1 to 2:1.

The intermediate having XCF$_2$CFYOSO$_2$—group in the process of the present invention is usually produced in the form of a mixture of several kinds of compounds with different —OSO$_2$— unit content. $^{19}$F-NMR spectroscopy showed that at least four kinds of compounds are included in the mixture. It has been observed that, when the molar ratio of sulfur trioxide in the reagent mixture to the polyfluoroethane is high, the ratio of compounds with higher —OSO$_2$—unit content increases. The intermediates can be isolated as a mixture from the reaction mixture. The mixture can be used in the next decomposition step to convert them into difluorohaloacetyl fluoride.

In the process of the present invention, the decomposition of the intermediate can be carried out just by heating. For example, the difluorohaloacetyl fluoride can be obtained at a yield of about 40 to 50% by heating the intermediate at 150° C. to 450° C. The yield can be increased by using a decomposition assistant, and thereby the temperature for the decomposition can be decreased to 0° C. to 200° C. Various decomposition assistants can be used, for example, sulfuric acid or fuming sulfuric acid is preferably used. It is especially preferable to use 100% sulfuric acid or fuming sulfuric acid or low sulfur trioxide content since the decomposition is preferably carried out under substantially anhydrous condition.

Suitable decomposition assistants include alkali metal halides, ammonium halides and quaternary ammonium halides, silver fluoride and alkali metal perfluoroalkoxides. Among them, the alkali metal halides such as potassium fluoride are preferably used considering their high activity and the case of availability.

In the decomposition reaction in which said decomposition assistant is used, it is preferable to carry out the reaction in an aprotic polar solvent wherein the decomposition assistant exhibits high activity and the increase of the yield of difluorohaloacetyl fluoride is obtained.

Suitable solvents include Sulfolane, Diglyme, Tetraglyme, dioxane, 1,2-dimethoxyethane and tetrahydrofuran (THF). The amount of the solvent is usually from 1 to 20 times the weight of the intermediate.

The decomposition reaction is preferably carried out under substantially anhydrous condition since the difluorohaloacetyl fluoride is easily hydrolyzed into difluorohaloacetic acid (XCF$_2$COOH), sometimes into oxyalic acid (HOOC—COOH) in the presence of moisture.

The present invention will be further illustrated by certain examples and references which are provided for purposes of illustration only.

EXAMPLE 1

In a three-necked flask equipped with a thermometer, a dropping funnel and a magnetic stirrer, 16.8 g. (0.11 mol) of bromine was charged and 16 g. (0.2 mol) of sulfur trioxide was added dropwise at room temperature in about 30 minutes. The resulting reagent mixture was charged into an autoclave and 11 g. (0.11 mol) of tetrafluoroethylene was added while stirring at 30° C. in about 2 hours. The conversion of tetrafluoroethylene was 99%. $^{19}$F-NMR spectroscopy showed that the reaction mixture contained intermediates having BrCF$_2$CF$_2$OSO$_2$— group with chemical shifts at $-69$ ppm and $-85$ to $-86$ ppm and 1,2-dibromotetrafluoroethane. It was confirmed that the selectivities to the products were 71% and 29% respectively.

Into a flask equipped with a thermometer, a reflux condenser and a magnetic stirrer, 28 g. of the intermediate 46 g. of 30% fuming sulfuric acid were charged and a decomposition was carried out at 100 to 110° C. for 10 hours. The reaction product was taken out from the top of the refluxing condenser and collected in a trap cooled to $-78°$ C. $^{19}$F-NMR spectroscopy showed the product to be difluorobromoacetyl fluoride with chemical shifts at 9.5 ppm (triplet) and $-62.6$ ppm (doublet). The conversion was 71% and the selectivity to difluorobromoacetyl fluoride was 95%.

EXAMPLE 2

Into a reactor used as in Example 1, 16.8 g. (0.11 mol) of bromine was charged and 34 g. (0.43 mol) of sulfur trioxide was added dropwise at room temperature in 1 hour. The resulting reagent mixture was charged into an autoclave and 11 g. (0.11 mol) of tetrafluoroethylene was added at 30° C. while stirring in about 2 hours. The conversion of tetrafluoroethylene was 99%. The identification of the reaction product was performed by $^{19}$F-NMR spectroscopy as in Example 1 to confirm that the selectivities to the intermediate having BrCF$_2$CF$_2$OSO$_2$— group, 1,2-dibromotetrafluoroethane and 2-hydroxytetrafluoroethane sulfonic acid sultone

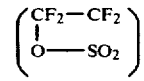

were 83%, 11% and 6% respectively.

EXAMPLE 3

The reagent mixture obtained from bromine and sulfur trioxide under the condition of Example 1 and 40 ml. of 1,2-dibromotetrafluoroethane were charged in an autoclave and the mixture was cooled to 0° C. and 11 g. (0.11 mol) of tetrafluoroethylene was added in about 2 hours. The conversion of tetrafluoromethylene was 90%. The selectivities to the intermediate having BrCF$_2$CF$_2$OSO$_2$— group and 1,2-dibromotetrafluoroethane were 80% and 20%, respectively.

EXAMPLE 4

Into a reactor used as in Example 1, 25 g. (0.10 mol) of iodine, and 40 ml. of 1,1,2-trichlorotrifluoroethane were charged and 8 g. (0.10 mol) of sulfur trioxide was added dropwise at room temperature in about 20 minutes. The resulting reagent mixture was charged into an autoclave and cooled to 0° C. and 10 g. (0.10 mol) of tetrafluoroethylene was added in about 5 hours. The conversion of tetrafluoroethylene was 58%. $^{19}$F-NMR spectroscopy showed that the reaction mixture contained intermediates having $ICF_2CF_2OSO_2-$ group with chemical shifts at $-65.3$ ppm and $-83.8$ to $-85.6$ ppm, 2-hydroxytetrafluoroethanesulfonic acid sultone and 1,2-diiodotetrafluoroethane. The selectivities to the products were 89%, 9% and 2%, respectively.

Into a flask equipped with a thermometer, a reflux condenser and a magnetic stirrer, 10 g. of the intermediates, 2.7 g. of potassium fluoride and 30 ml. of sulfolane were charged and heated at 50° C. for 6 hours while stirring and then the temperature was raised to 80° C. and heated for 2 hours to decompose the intermediate. The reaction product was taken out from the top of the refluxing condenser and collected in a trap cooled at $-78°$ C. The conversion was 95% and the selectivity to difluoroiodoacetyl fluoride was 97%.

EXAMPLE 5

In accordance with the process of Example 1, the reaction of 13.0 g. of chlorotrifluoroethylene with the reagent mixture of 16.8 g. of bromine and 16.0 g. of sulfur trioxide, was carried out. The conversion of chlorotrifluoroethylene was 95% and the reaction mixture contained 11.7 g. of the intermediate having $BrCF_2CFClOSO_2-$ group.

After distilling off the unreacted bromine and 1,2-dibromoethane, the remaining bottom containing 10 g. of intermediates was mixed with 18 g. of 30% fuming sulfuric acid and heated. The decomposition and the condensation of the product and the analysis were carried out as in Example 1 and the production of 3.2 g. of difluorobromoacetyl fluoride was confirmed.

We claim

1. A process for producing a difluorohaloacetyl fluoride which comprises the steps of:
   (a) producing an intermediate having a group of the formula

$XCF_2CFYOSO_2-$ wherein X is I or Br, Y is F, Cl, Br or I; by reacting a polyfluoroethylene of the formula

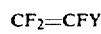

$CF_2=CFY$ with a reagent obtained by mixing sulfur trioxide with a halogen selected from iodine and bromine; and
   (b) decomposing said intermediate into said product.
2. The process according to claim 1 wherein said polyfluoroethylene is tetrafluoroethylene.
3. The process according to claim 1 wherein said polyfluoroethylene is chlorotrifluoroethylene.
4. The process according to claim 1 wherein a molar ratio of sulfur trioxide to a halogen in said reagent mixture is in a range of 1:1 to 5:1.
5. The process according to claim 1 wherein a molar ratio of halogen in said reagent mixture to polyfluoroethylene in said reaction is in a range of 0.5:1 to 2:1.
6. The process according to claim 1 wherein said reaction of said polyfluoroethylene with said reagent mixture is carried out at a temperature ranging from $-20°$ C. to $+150°$ C.
7. The process according to claim 1 wherein said decomposition of said intermediate is carried in the presence of a decomposition assistant.
8. The process according to claim 7 wherein said decomposition assistant is sulfuric acid or fuming sulfuric acid.
9. The process according to claim 7 wherein said decomposition assistant is an alkali metal halide.
10. The process according to claim 7 wherein a molar ratio of said decomposition assistant to said intermediate is in a range of 0.1 to 10.
11. The process according to claim 7 wherein said decomposition of said intermediate is carried out at a temperature ranging from 0° C. to 200° C.

* * * * *